(12) United States Patent
Maruhata

(10) Patent No.: US 9,456,929 B2
(45) Date of Patent: Oct. 4, 2016

(54) SHEET ARTICLE MANUFACTURING APPARATUS

(75) Inventor: Kazuya Maruhata, Mima-gun (JP)

(73) Assignee: LIVEDO CORPORATION, Shikokuchou-shi (JP)

( * ) Notice: Subject to any disclaimer, the term of this patent is extended or adjusted under 35 U.S.C. 154(b) by 453 days.

(21) Appl. No.: 14/128,904

(22) PCT Filed: Jul. 5, 2012

(86) PCT No.: PCT/JP2012/004389
§ 371 (c)(1),
(2), (4) Date: Dec. 23, 2013

(87) PCT Pub. No.: WO2013/008433
PCT Pub. Date: Jan. 17, 2013

(65) Prior Publication Data
US 2014/0124143 A1    May 8, 2014

(30) Foreign Application Priority Data
Jul. 8, 2011 (JP) ................. 2011-151580

(51) Int. Cl.
*A61F 13/00* (2006.01)
*A61F 13/15* (2006.01)
*B05C 1/08* (2006.01)
(Continued)

(52) U.S. Cl.
CPC ... *A61F 13/00991* (2013.01); *A61F 13/15658* (2013.01); *A61F 13/15764* (2013.01); *A61F 13/15804* (2013.01); *B05C 1/0808* (2013.01); *B05C 1/0813* (2013.01); *B05C 1/10* (2013.01);
(Continued)

(58) Field of Classification Search
None
See application file for complete search history.

(56) References Cited

U.S. PATENT DOCUMENTS 3,759,011 A  9/1973  Akke
4,604,852 A  8/1986  Becker
(Continued)

FOREIGN PATENT DOCUMENTS

CN    1988864 A    6/2007
CN   101032436 A    9/2007
(Continued)

OTHER PUBLICATIONS

International Search Report, dated Oct. 15, 2012, issued in application No. PCT/JP2012/004386. (4 pages).
(Continued)

*Primary Examiner* — Barbara J Musser
(74) *Attorney, Agent, or Firm* — Westerman, Hattori, Daniels & Adrian, LLP

(57) ABSTRACT

In an absorbent sheet manufacturing apparatus, a first roller (31) and a third roller (51) are rotated while each first concave portion (312) faces a convex portion (512), and therefore sheet concave portion rows (913) are formed on a first sheet member (91). The first sheet member (91) is transferred from a first roller-outer side surface (311) to a cylinder-outer side surface (211) of a supply cylinder (21), and a lower portion of the cylinder-outer side surface (211) is in contact with the first sheet member (91) while supply concave portions (212) supplied with particles face the sheet concave portion rows (913). Therefore, particles can be supplied accurately into each sheet concave portion (912) included in the sheet concave portion rows (913) and be held in the sheet concave portion (912) while the particles are practically prevented from scattering to the outside of the sheet concave portion (912).

13 Claims, 10 Drawing Sheets

(51) Int. Cl.
*B05C 1/10* (2006.01)
*B05C 1/16* (2006.01)
*B05C 19/00* (2006.01)
*B05C 19/06* (2006.01)

(52) U.S. Cl.
CPC ............. *B05C 1/16* (2013.01); *B05C 19/00* (2013.01); *B05C 19/06* (2013.01)

(56) References Cited

U.S. PATENT DOCUMENTS

| | | | |
|---|---|---|---|
| 5,494,622 | A | 2/1996 | Heath et al. |
| 2006/0021695 | A1 | 2/2006 | Blessing et al. |
| 2006/0278335 | A1 | 12/2006 | Moriura et al. |
| 2010/0213231 | A1 | 8/2010 | Yamamoto |

FOREIGN PATENT DOCUMENTS

| | | |
|---|---|---|
| EP | 1621167 A2 | 2/2006 |
| EP | 1655007 A1 | 5/2006 |
| EP | 1700586 A2 | 9/2006 |
| EP | 2444044 A1 | 4/2012 |
| JP | 2002-345883 A | 12/2002 |
| JP | 2005-059579 A | 3/2005 |
| JP | 2007-130818 A | 5/2007 |
| JP | 2008-507384 A | 3/2008 |
| KR | 10-2011-0129447 A | 12/2011 |
| WO | 2006/015138 A1 | 2/2006 |
| WO | 2006-015141 A2 | 2/2006 |

OTHER PUBLICATIONS

Written Opinion, dated Oct. 15, 2012, issued in application No. PCT/JP2012/004386. (4 pages).
International Search Report of PCT/JP2012/004387, mailing date of Oct. 9, 2012. (3 pages).
Written Opinion of PCT/JP2012/004387, mailing date of Oct. 9, 2012. (4 pages).
International Search Report for PCT/JP2012/004389, Mailing Date of Oct. 9, 2012.
Written Opinion for PCTJP2012/004389, Mailing Date of Oct. 9, 2012.

SHEET ARTICLE MANUFACTURING APPARATUS

TECHNICAL FIELD

The present invention relates to a sheet article manufacturing apparatus for manufacturing a sheet article for an absorbent article.

BACKGROUND ART

In an absorbent article such as an absorbent pad for light incontinence which is used by being attached on the inside of a disposable diaper, an absorbent sheet is conventionally utilized which is obtained by sandwiching particles of high-absorbent resin between two sheet members formed of nonwoven fabric or the like to fix the particles therebetween.

Japanese Patent Application Laid-Open No. 2007-130818 (Document 1) is related to a composite sheet. In the composite sheet, a plurality of concave portions are formed on one of two sheets, and functional material such as absorbent polymer is held in the concave portions. In a manufacturing apparatus for the composite sheet of Document 1, a first sheet is supplied to an engaging region between two rolls having concave-convex shapes engaging with each other, and the first sheet is held along the concave-convex shape on a periphery of a first roll by exerting a suction force on the first sheet. Subsequently, by exerting the suction force through the first sheet, functional material stored in a duct facing the first roll is held on the first sheet. Then, a second sheet is laid and bonded on the first sheet, to complete the composite sheet.

International Publication No. WO 2006/15141 (Document 2) is related to a process of producing sandwich structures with particulate material pattern. In an apparatus of Document 2, after adhesive is applied onto a carrier material, indentations are formed in the carrier material. Particulate material expelled from one of recesses of a transfer device is transferred into a corresponding indentation, and then, a cover material is overlaid and bonded on the carrier material.

Incidentally, in the manufacturing apparatus of Document 1, since functional material in the duct is supplied onto the first sheet by gravity and air blow, the functional material is supplied on not only the concave portions of the first sheet but also portions of the first sheet other than the concave portions. Thus, it is difficult to produce a composite sheet where existence regions of the functional material are arranged in a dotted pattern. The functional material is held on the first sheet with the suction force by the first roll until the first sheet which has passed through the duct is covered with the second sheet. However, since a rotation speed of the roll is normally high in such apparatus, scattering of the functional material from the first sheet may occur by a centrifugal force.

In the apparatus of Document 2, the particulate material is expelled toward the carrier material from the transfer device. Thus, when the particulate material collides with the carrier material, the particulate material may scatter to the outside of the indentations. Since adhesive is applied on the carrier material in advance, a distance between the transfer device and the carrier material can't be decreased below a certain value.

SUMMARY OF INVENTION

The present invention is intended for a sheet article manufacturing apparatus for manufacturing a sheet article for an absorbent article. It is a main object of the present invention to supply particles into a sheet concave portion row accurately and hold the particles in the sheet concave portion row.

A preferred sheet article manufacturing apparatus according to the present invention comprises: a sheet concave portion forming part for sequentially forming sheet concave portions of a sheet concave portion row on a first sheet member along a conveying direction of the first sheet member, the first sheet member being continuous sheet; a supply cylinder which has a plurality of supply concave portions arranged on an cylinder-outer side surface in a circumferential direction, the supply cylinder being rotated around a cylinder rotation axis along a horizontal direction, a lower portion of the cylinder-outer side surface being in contact with the first sheet member so that each supply concave portion faces a sheet concave portion, to sequentially supply particles of absorbent material or deodorant material from the plurality of supply concave portions to the sheet concave portions of the sheet concave portion row; a particle filling part for sequentially filling the plurality of supply concave portions with the particles; and a sheet bonding part for placing a second sheet member on the sheet concave portion row which has been supplied with the particles to bond the second sheet member on the first sheet member, the second sheet member being continuous sheet; wherein the sheet concave portion forming part comprises: a first roller which has a plurality of first concave portions arranged on a first roller-outer side surface in a circumferential direction, the first roller being in contact with the supply cylinder through the first sheet member and being rotated around a rotation axis parallel to the cylinder rotation axis so that each first concave portion faces a supply concave portion, to transfer the first sheet member from the first roller-outer side surface to the cylinder-outer side surface; and a concave portion forming part for sequentially forming the sheet concave portions by causing portions of the first sheet member to be recessed into first concave portions; the sheet bonding part comprises: a second roller which has a plurality of second concave portions arranged on a second roller-outer side surface in a circumferential direction, the second roller being in contact with the supply cylinder through the first sheet member where the particles has been supplied in the sheet concave portion row and being rotated around a rotation axis parallel to the cylinder rotation axis so that each second concave portion faces a supply concave portion, to transfer the first sheet member from the cylinder-outer side surface to the second roller-outer side surface; and a second sheet supplying part for supplying the second sheet member onto the first sheet member positioned on the second roller-outer side surface. In the sheet article manufacturing apparatus, it is possible to supply particles into a sheet concave portion row accurately and hold the particles in the sheet concave portion row.

In this case, since the concave portion forming part comprises a suction part for suctioning the first sheet member from the inside of the first roller through the plurality of first concave portions, the sheet concave portion row formed in the plurality of first concave portions can be maintained.

The concave portion forming part may comprise a third roller which has a plurality of convex portions arranged on a third roller-outer side surface in a circumferential direction, the third roller being rotated around a rotation axis parallel to the cylinder rotation axis so that each convex portion faces a first concave portion, to depress a portion of the first sheet member toward the first concave portion by the each convex portion. In this case, the third roller comprises a convex portion heating part for heating the plurality of convex portions, and therefore the first sheet member can be deformed easily when depressed by the convex portion.

Another preferred sheet article manufacturing apparatus according to the present invention comprises: a supply cylinder which has a plurality of supply concave portions arranged on an cylinder-outer side surface in a circumferential direction, the supply cylinder being rotated around a cylinder rotation axis along a horizontal direction, a lower portion of the cylinder-outer side surface being in contact with a first sheet member to sequentially supply particles of absorbent material or deodorant material from the plurality of supply concave portions onto the first sheet member; a particle filling part for sequentially filling the plurality of supply concave portions with the particles; and a sheet bonding part for placing a second sheet member on particles of absorbent material or deodorant material which has been supplied on the first sheet member by the supply cylinder to bond the second sheet member on the first sheet member, the second sheet member being continuous sheet; wherein the sheet bonding part comprises: a roller which has a plurality of suction ports arranged on a roller-outer side surface in a circumferential direction, the roller being in contact with the supply cylinder through the first sheet member which has been supplied with the particles and being rotated around a rotation axis parallel to the cylinder rotation axis so that suction ports face supply concave portions, to transfer the first sheet member from the cylinder-outer side surface to the roller-outer side surface; a suction part for holding the particles by suctioning the particles from the inside of the roller through the suction ports and the first sheet member; and a second sheet supplying part for supplying the second sheet member onto the first sheet member positioned on the roller-outer side surface. In the sheet article manufacturing apparatus, it is possible to easily manufacture a sheet article for an absorbent article where particles are arranged in a dotted pattern.

These and other objects, features, aspects and advantages of the present invention will become more apparent from the following detailed description of the present invention when taken in conjunction with the accompanying drawings.

DESCRIPTION OF EMBODIMENTS

Figure 1:
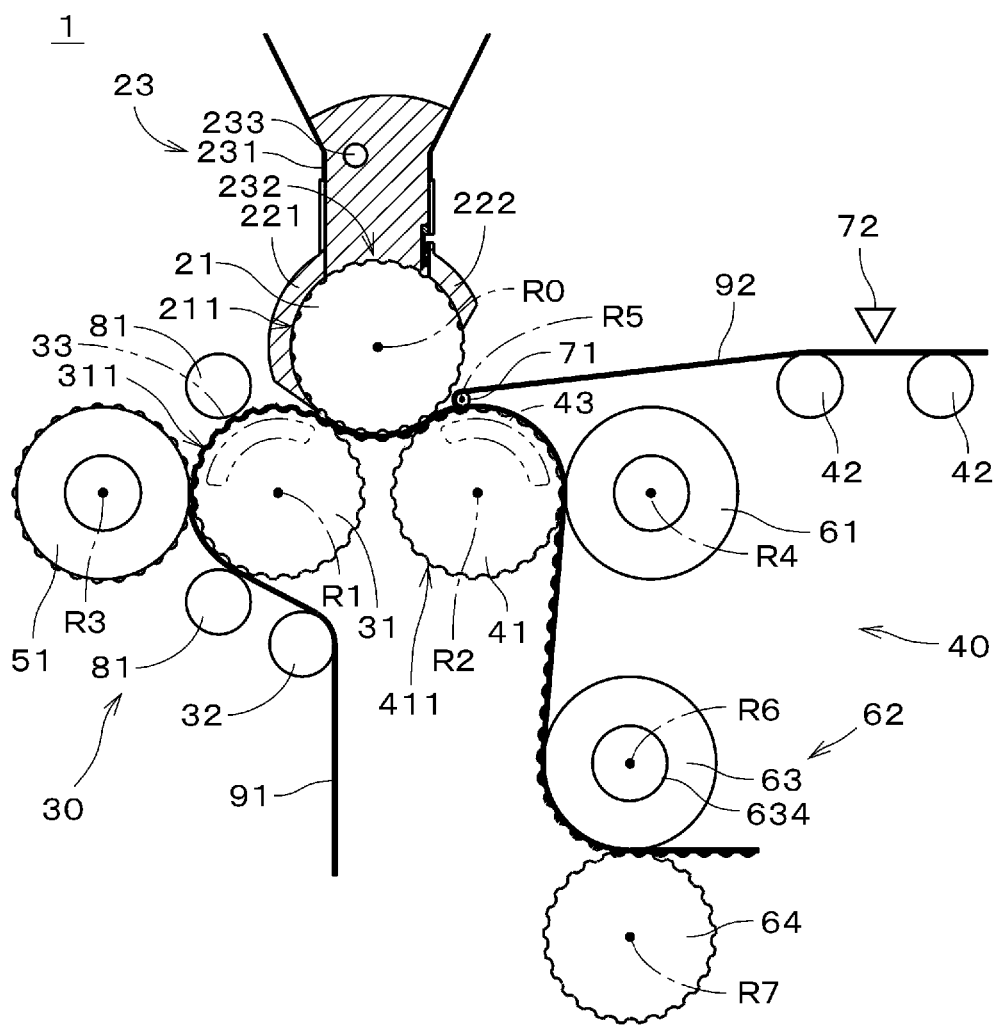
FIG. 1 is a view showing an absorbent sheet manufacturing apparatus in accordance with a first preferred embodiment.

FIG. 1 is a view showing an absorbent sheet manufacturing apparatus 1 in accordance with a first preferred embodiment of the present invention. The absorbent sheet manufacturing apparatus 1 is one sheet article manufacturing apparatus for manufacturing a sheet article for an absorbent article and manufactures absorbent sheets by sandwiching particles of high-absorbent resin such as SAP (Super Absorbent Polymer) between sheet members formed of nonwoven fabric or the like. The absorbent sheet is a sheet article used for an absorbent article such as a disposable diaper or absorbent pad for light incontinence.

The absorbent sheet manufacturing apparatus 1 has a supply cylinder 21 which is a generally cylindrical member around (with its center lying on) a cylinder rotation axis R0 along (toward) a horizontal direction, a first roller 31 located to the lower-left of the supply cylinder 21, a second roller 41 located to the lower-right of the supply cylinder 21, a third roller 51 located to the left of the first roller 31, a fourth roller 61 located to the right of the second roller 41, and a sheet conveying roller 71 located above the second roller 41 and close to the second roller 41 and the supply cylinder 21. In FIG. 1, hatching lines aren't drawn in the cross sections of supply cylinder 21 and the rollers in order to facilitate understanding of the drawing (the same applies to some other drawings).

The first roller 31 has a generally cylindrical shape around a rotation axis R1 parallel to a direction along the cylinder rotation axis R0 (hereinafter, the direction is referred to as an "axial direction"), and the second roller 41 has a generally cylindrical shape around a rotation axis R2 parallel to the axial direction. The first roller 31 and the second roller 41 have structures similar to each other, and are arranged symmetrically with respect to a plane including the cylinder rotation axis R0 of the supply cylinder 21 and being parallel to the vertical direction (direction of gravitational force). The third roller 51 and the fourth roller 61 have generally columnar shapes around rotation axes R3, R4 parallel to the axial direction, respectively. The sheet conveying roller 71 has a generally columnar shape around a rotation axis R5 parallel to the axial direction.

The absorbent sheet manufacturing apparatus 1 further has an auxiliary bonding part 62 located under the fourth roller 61. The auxiliary bonding part 62 has a first auxiliary bonding roller 63 which has a generally columnar shape around a rotation axis R6 parallel to the axial direction, and a second auxiliary bonding roller 64 which has a generally columnar shape around a rotation axis R7 parallel to the axial direction. The absorbent sheet manufacturing apparatus 1 has a pair of nip rollers 81 (i.e., two nip rollers 81) which are located to the upper-left and the lower-left of the first roller 31. Each nip roller 81 has a generally columnar shape around a central axis parallel to the axial direction. Furthermore, the absorbent sheet manufacturing apparatus 1 has a plurality of auxiliary rollers 32, 42 each having a generally columnar shape around a central axis parallel to the axial direction, and an applying part 72 located above the auxiliary rollers 42.

The supply cylinder 21, the third roller 51, the fourth roller 61, the sheet conveying roller 71 and the first auxiliary bonding roller 63 are rotated in a counterclockwise direction in FIG. 1, and the first roller 31, the second roller 41 and the second auxiliary bonding roller 64 are rotated in a clockwise direction in FIG. 1.

In the absorbent sheet manufacturing apparatus 1, (each portion of) a first sheet member 91, which is continuous sheet formed of nonwoven fabric or the like, is conveyed to the first roller 31 through the auxiliary roller 32, and passes between the first roller 31 and the lower nip roller 81. Subsequently, the first sheet member 91 passes between the first roller 31 and the third roller 51, and passes between the first roller 31 and the upper nip roller 81. The first roller 31 is in contact through the first sheet member 91 with the third roller 51, and the first sheet member 91 is sandwiched between the first roller 31 and the third roller 51. Therefore, sheet concave portions of each sheet concave portion row 913 (see FIG. 15) are sequentially formed on the first sheet member 91 along a conveying direction of the first sheet member 91 as described later. In the following description, constituents for forming the sheet concave portion rows 913, such as the first roller 31 and the third roller 51, are referred to collectively as a sheet concave portion forming part 30.

The first sheet member 91 is transferred from a first roller-outer side surface 311 of the first roller 31 to a cylinder-outer side surface 211 of the supply cylinder 21, and particles of high-absorbent resin (hereinafter, simply referred to as "particles") are sequentially supplied by the supply cylinder 21 into sheet concave portions of the sheet concave portion rows 913 on the first sheet member 91. The first sheet member 91 is further transferred from the cylinder-outer side surface 211 of the supply cylinder 21 to a second roller-outer side surface 411 of the second roller 41.

On the other hand, a second sheet member 92, which is continuous sheet formed of nonwoven fabric or the like, is led to the sheet conveying roller 71 through the auxiliary rollers 42. Adhesive (in the present embodiment, hot melt adhesive) is applied by the applying part 72 almost over the entire surface of one main surface of the second sheet member 92. The second sheet member 92 is led from the sheet conveying roller 71 to the second roller 41, and is supplied onto the first sheet member 91 lying on the second roller-outer side surface 411 of the second roller 41. In other words, the sheet conveying roller 71 is a second sheet supplying part for supplying the second sheet member 92 onto the first sheet member 91. The laminated (layered) first sheet member 91 and second sheet member 92 pass between the second roller 41 and the fourth roller 61, and then pass between the first auxiliary bonding roller 63 and the second auxiliary bonding roller 64. Therefore, the first sheet member 91 and the second sheet member 92 are bonded with each other, and an absorbent sheet is formed. In the following description, constituents for bonding the first sheet member 91 and the second sheet member 92, such as the second roller 41, the fourth roller 61, the sheet conveying roller 71 and the auxiliary bonding part 62 including the first auxiliary bonding roller 63 and the second auxiliary bonding roller 64, are referred to collectively as a sheet bonding part 40.

A particle filling part 23 is provided above the supply cylinder 21. The particle filling part 23 has a particle tank 231 which is located above the supply cylinder 21 and which stores the particles, and a level sensor 233 provided to the particle tank 231. When the level sensor 233 detects that the amount of particles stored in the particle tank 231 becomes equal to or less than a certain level, particles are replenished into the particle tank 231. The particle tank 231 extends almost in parallel with the vertical direction, and a particle filling opening 232 facing the cylinder-outer side surface 211 of the supply cylinder 21 is provided at a lower end of the particle tank 231. The particle filling opening 232 faces a portion including the uppermost portion of the supply cylinder 21.

A first cover part 221 which covers a portion of the cylinder-outer side surface 211 of the supply cylinder 21 and a second cover part 222 which covers another portion of the cylinder-outer side surface 211 are provided around the supply cylinder 21. The first cover part 221 spreads from the particle filling opening 232 to a vicinity of a portion where the supply cylinder 21 is closest to the first roller 31 along the rotation direction of the supply cylinder 21 (i.e., in the counterclockwise direction in FIG. 1), to cover the cylinder-outer side surface 211 in the left side of the supply cylinder 21. The second cover part 222 spreads from the particle filling opening 232 to a vicinity of a right end portion of the supply cylinder 21 along an opposite direction of the rotation direction of the supply cylinder 21 (i.e., toward the posterior side in the rotation direction (that is, in the clockwise direction in FIG. 1)), to cover the cylinder-outer side surface 211 in the right side of the supply cylinder 21.

Figure 2:
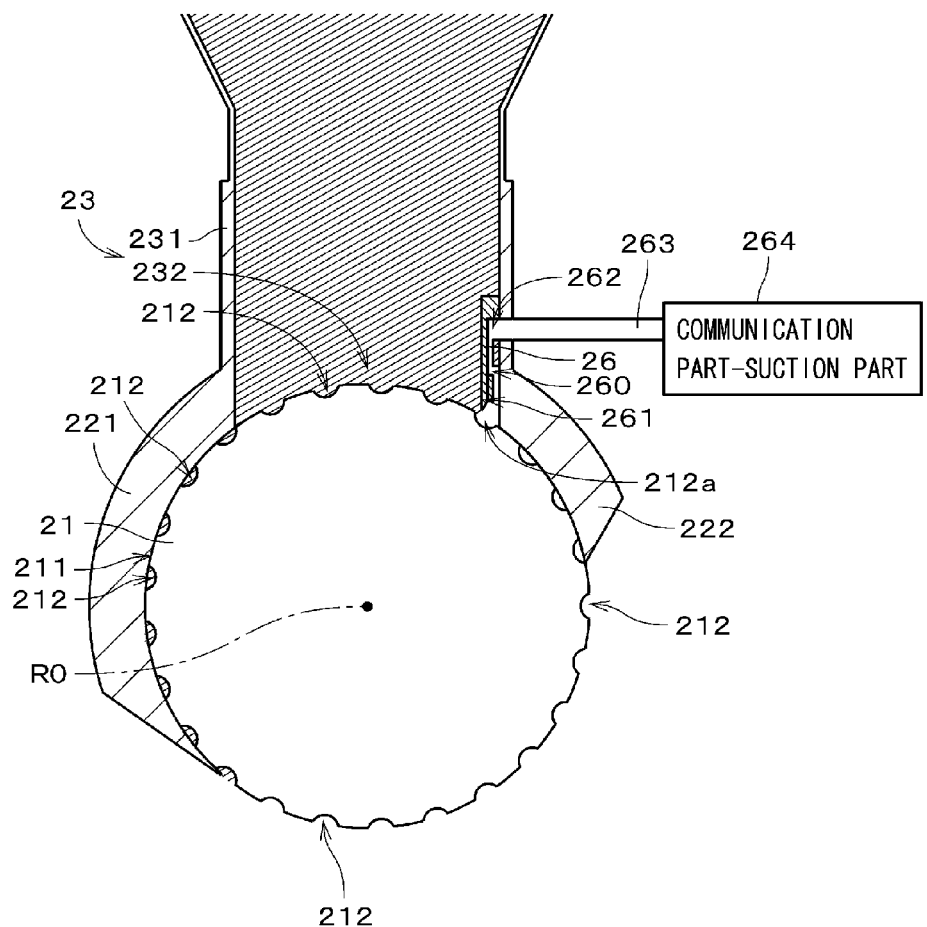
FIG. 2 is a cross-sectional view of a vicinity of a supply cylinder.
Figure 3:
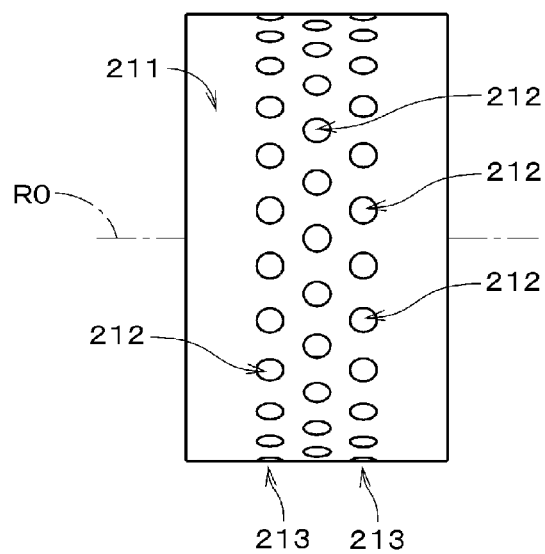
FIG. 3 is a front view of the supply cylinder.

FIG. 2 is an enlarged cross-sectional view showing the vicinity of the supply cylinder 21, and shows a cross section which is orthogonal to the cylinder rotation axis R0. FIG. 3 is a view showing the cylinder-outer side surface 211 of the supply cylinder 21, and in FIG. 3, an appearance of the cylinder-outer side surface 211 which is observed along a direction orthogonal to the cylinder rotation axis R0 is shown. In FIG. 2, regions of the particles are densely hatched. In FIG. 3, the first cover part 221 and the second cover part 222 are omitted.

As shown in FIGS. 2 and 3, with respect to each of a plurality of positions in the axial direction, a plurality of supply concave portions 212 are arranged at regular intervals on (in) the cylinder-outer side surface 211 in a circumferential direction around the cylinder rotation axis R0 so as to be away from each other. When the plurality of supply concave portions 212 which are arranged in the circumferential direction at the same position in the axial direction are referred to as a supply concave portion row 213, three supply concave portion rows 213 are provided in the supply cylinder 21 as shown in FIG. 3. In the present embodiment, the shape of each supply concave portion 212 observed along a direction orthogonal to the cylinder rotation axis R0 is generally circular. In a cross section orthogonal to the cylinder rotation axis R0, the shape of a bottom surface of each supply concave portion 212 is generally arc-like as shown in FIG. 2. The supply concave portions 212 may have a various shape, for example, the shape of each supply concave portion 212 observed along a direction orthogonal to the cylinder rotation axis R0 may be generally rectangular. Also the shape of each supply concave portion 212 in a cross section orthogonal to the cylinder rotation axis R0 may be generally rectangular. On the cylinder-outer side surface 211, one, two, four or more supply concave portion rows 213 may be provided. In each supply concave portion row 213, the plurality of supply concave portions 212 aren't arranged necessarily at regular intervals.

The cylinder-outer side surface 211 of the supply cylinder 21 is very close to an inner side surface of the first cover part 221 and an inner side surface of the second cover part 222 in a region where the supply concave portions 212 don't exist, and the cylinder-outer side surface 211 is practically in contact with them.

In the absorbent sheet manufacturing apparatus 1, the supply cylinder 21 is rotated around the cylinder rotation axis R0 at a high speed, and particles are sequentially filled from the particle tank 231 of the particle filling part 23 into the plurality of supply concave portions 212 passing the particle filling opening 232, due to gravity. A communication part 26 located adjacent to the particle filling opening 232 is provided to the right of the particle filling opening 232 in FIG. 2 (i.e., posterior to the particle filling opening 232 in the rotation direction of the supply cylinder 21). The communication part 26 is provided across almost the entire extent where the three supply concave portion rows 213 (see FIG. 3) are arranged in the axial direction of the supply cylinder 21.

A supply concave portion 212a out of the plurality of supply concave portions 212 (the supply concave portion is denoted by a reference sign 212a in order to be distinguished from the other supply concave portions 212), which faces a posterior edge of the particle filling opening 232 (i.e., a posterior end in the rotation direction of the supply cylinder 21) in the supply cylinder 21, is brought into communication with external space by the communication part 26. Therefore, when particles are filled into the supply concave portion 212a from the particle filling part 23, air in the supply concave portion 212a is forced out by particles entering the supply concave portion 212a and is easily discharged to the external space through the communication part 26. As a result, it is possible to increase a density of particles filled in the supply concave portion 212a.

In the communication part 26, a first end portion 261 is one end portion which faces the supply cylinder 21, and the first end portion 261 is positioned below a second end portion 262 which is the other end portion located on the external space side of the communication part 26. A communication path 260 of the communication part 26 has at least two bending portions (i.e., the communication path 260 bends at least two points). In the present embodiment, the communication path 260 has three bending portions, and the first end portion 261 of the communication part 26 is almost right below the second end portion 262 in the vertical direction. This can reduce escape of particles from the supply concave portion 212a to the external space through the communication part 26.

A communication part-suction part 264 for suctioning gas in the communication part 26 is connected to the second end portion 262 of the communication part 26 through a pipe 263. The communication part-suction part 264 has a regulator for adjusting a suction pressure and performs suction weakly. Thus, air in the supply concave portion 212a is discharged more efficiently and therefore, the density of particles filled in the supply concave portion 212a can be increased further.

Figure 4:
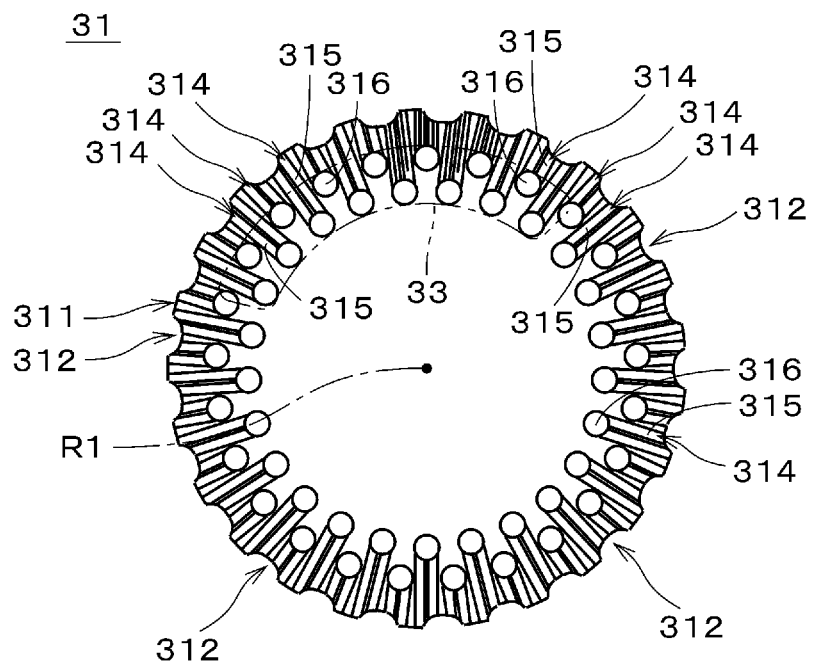
FIG. 4 is a cross-sectional view of a first roller.
Figure 5:
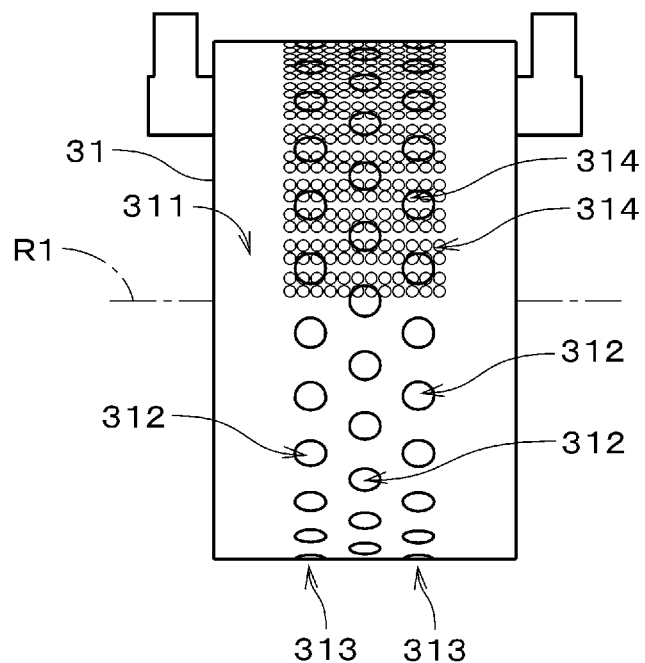
FIG. 5 is a front view of the first roller.

FIG. 4 is a cross-sectional view of the first roller 31, and shows a cross section which is orthogonal to the rotation axis R1. FIG. 5 is a view showing the first roller-outer side surface 311 of the first roller 31, and in FIG. 3, an appearance of the first roller-outer side surface 311 which is observed along a direction orthogonal to the rotation axis R1 is shown. With respect to each of the plurality of positions in the axial direction, a plurality of first concave portions 312 are arranged on the first roller-outer side surface 311 in a circumferential direction around the rotation axis R1 so as to be away from one another. When the plurality of first concave portions 312 which are arranged in the circumferential direction at the same position in the axial direction are referred to as a first concave portion row 313, three first concave portion rows 313 are provided in the first roller 31 as shown in FIG. 5. In the present embodiment, the shape of each first concave portion 312 observed along a direction orthogonal to the rotation axis R1 is generally circular. In a cross section orthogonal to the rotation axis R1, the shape of a bottom surface of each first concave portion 312 is generally arc-like as shown in FIG. 4.

In the first roller 31, as shown in FIGS. 4 and 5, a plurality of first suction ports 314 are provided on the first roller-outer side surface 311. The shape of each first suction port 314 observed along a direction orthogonal to the rotation axis R1 is generally circular, and the first suction port 314 is sufficiently-small in comparison with the first concave portion 312. The first suction ports 314 are provided across the entire circumference of the first roller-outer side surface 311 in the circumferential direction around the rotation axis R1. In FIG. 5, only first suction ports 314 lying above the rotation axis R1 are drawn by thin lines in order to facilitate understanding of the drawing (the same applies to FIG. 8). The plurality of first suction ports 314 are provided across the three first concave portion rows 313 (from one side to the other side) in the axial direction. In other words, the plurality of first suction ports 314 are overlapped with a whole region where the plurality of first concave portion rows 313 are disposed, and naturally they are also provided in the inside of each first concave portion 312. As shown in FIG. 4, a first suction pipe 315 extends from each first suction port 314 toward the rotation axis R1.

Figure 6:
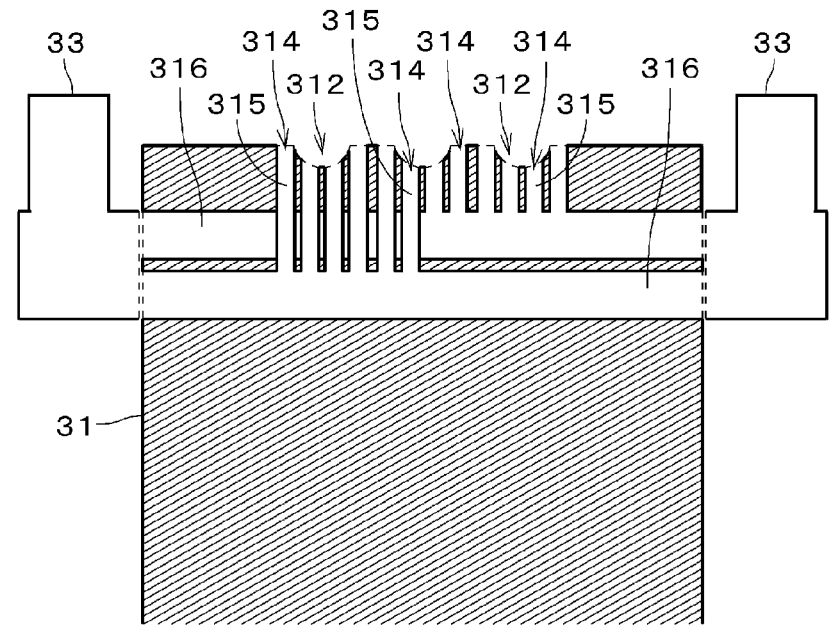
FIG. 6 is a view showing a pipe arrangement in the inside of the first roller.

FIG. 6 is a view showing a pipe arrangement in the inside of an upper portion of the first roller 31. The plurality of first suction pipes 315 extending from the plurality of first suction ports 314 are connected to common pipes 316 extending in the axial direction. In FIG. 6, hatching lines are drawn in portions other than the first suction pipes 315 and the common pipes 316 in the first roller 31, and portions overlapping with the first suction ports 314 in a cross section of each first concave portion 312 are drawn by broken lines in order to facilitate understanding of the drawing. The common pipes 316 each extending in the axial direction from one end to the other end of the first roller 31 are connected to first suction parts 33 provided to the both sides of the first roller 31 in the axial direction. The first suction parts 33 are supported by supporting members not shown, and aren't rotated together with the first roller 31. In the present embodiment, the first suction parts 33 are located slightly away from the first roller 31, and air in the common pipes 316 is suctioned by the first suction parts 33 performing suction of air.

As shown by chain double-dashed lines in FIG. 1, the first suction parts 33 extend from a vicinity of a position where the first roller 31 is in contact with the third roller 51 through the first sheet member 91 (so as to sandwich the first sheet member 91 therebetween), toward an anterior side of the rotation direction of the first roller 31 (i.e., in the clockwise direction in FIG. 1), to reach a vicinity of a position where the first roller 31 is in contact with the supply cylinder 21 through the first sheet member 91. In the first roller 31, as shown in FIG. 4, only some first suction ports 314 which are connected to common pipes 316 facing (i.e., substantially connecting) the first suction parts 33 with a small gap therebetween, perform suction, in the plurality of first suction ports 314.

Figure 7:
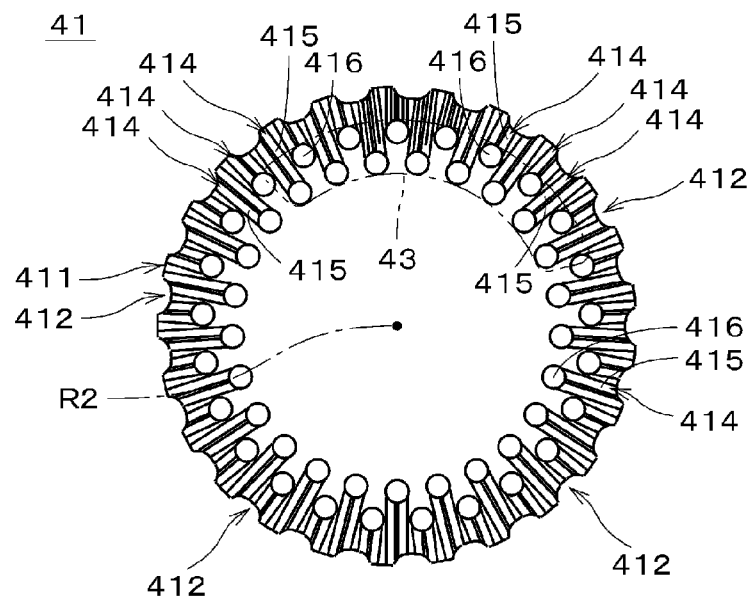
FIG. 7 is a cross-sectional view of a second roller.
Figure 8:
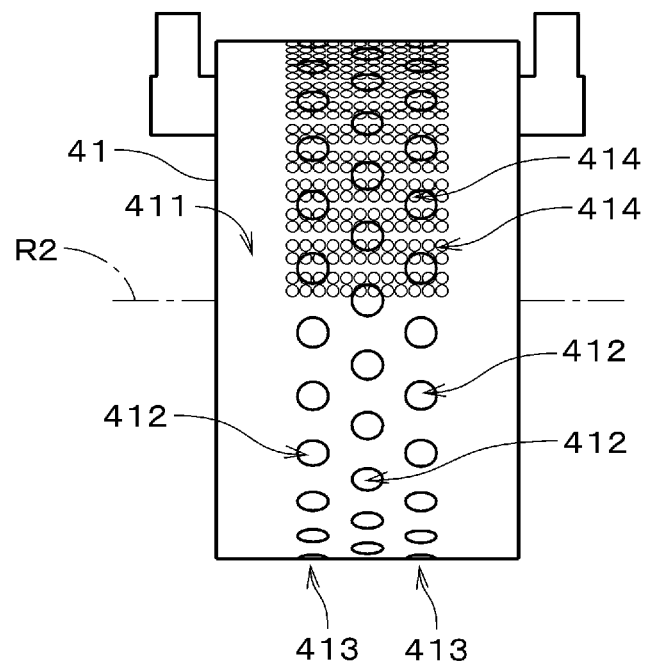
FIG. 8 is a front view of the second roller.

FIG. 7 is a cross-sectional view of the second roller 41, and shows a cross section which is orthogonal to the rotation axis R2. FIG. 8 is a view showing the second roller-outer side surface 411 of the second roller 41, and in FIG. 8, an appearance of the second roller-outer side surface 411 which is observed along a direction orthogonal to the rotation axis R2 is shown. The second roller 41 has a similar structure to the first roller 31. Specifically, with respect to each of the plurality of positions in the axial direction, a plurality of second concave portions 412 are arranged on the second roller-outer side surface 411 in a circumferential direction around the rotation axis R2 so as to be away from one another. In the second roller 41, as shown in FIG. 8, three second concave portion rows 413 are provided.

In the second roller-outer side surface 411, a plurality of second suction ports 414 are provided so as to overlap with a whole region where the plurality of second concave portion rows 413 are disposed. As shown in FIG. 7, a second suction pipe 415 extends from each second suction port 414 toward the rotation axis R2 to be connected to a common pipe 416. The common pipes 416 are connected to second suction parts 43 provided to the both sides of the second roller 41 in the axial direction. As shown by chain double-dashed lines in FIG. 1, the second suction parts 43 extend from a vicinity of a position where the second roller 41 is in contact with the supply cylinder 21 through the first sheet member 91, toward an anterior side of the rotation direction of the second roller 41 (i.e., in the clockwise direction in FIG. 1), to reach a vicinity of a position where the second roller 41 is in contact with the fourth roller 61 through the first sheet member 91. In the second roller 41, as shown in FIG. 7, only some second suction ports 414 which are connected to common pipes 416 facing the second suction parts 43 with a small gap therebetween, perform suction, in the plurality of second suction ports 414.

Figure 9:
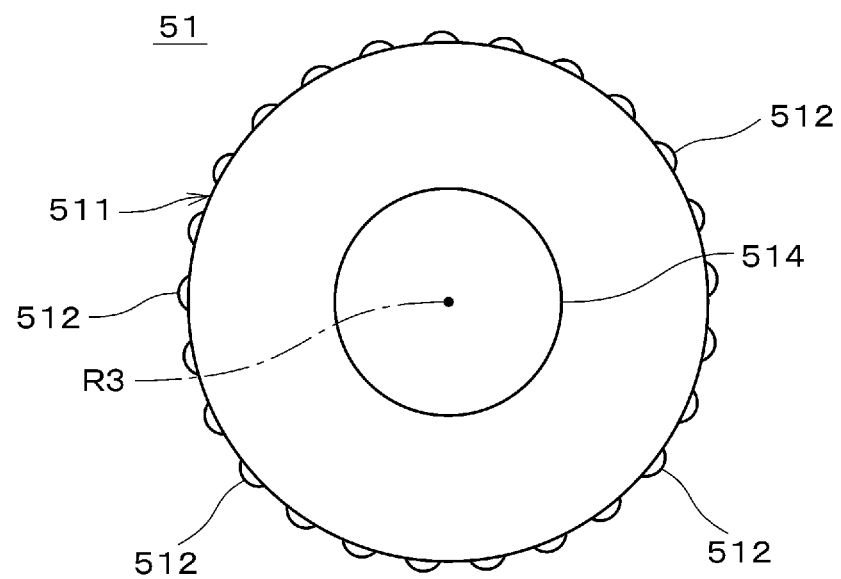
FIG. 9 is a cross-sectional view of a third roller.
Figure 10:
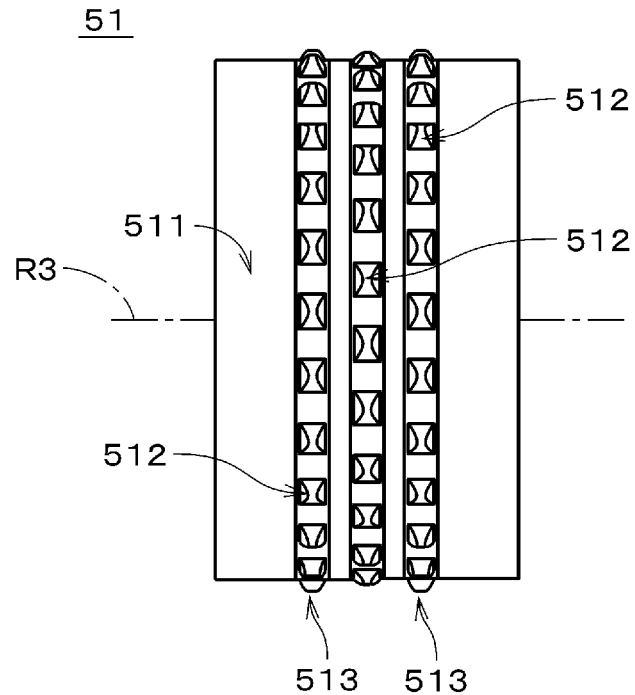
FIG. 10 is a front view of the third roller.

FIG. 9 is a cross-sectional view of the third roller 51, and shows a cross section which is orthogonal to the rotation axis R3. FIG. 10 is a view showing the third roller-outer side surface 511 of the third roller 51, and in FIG. 10, an appearance of the third roller-outer side surface 511 which is observed along a direction orthogonal to the rotation axis R3 is shown. With respect to each of the plurality of positions in the axial direction, a plurality of convex portions 512 are arranged on the third roller-outer side surface 511 of the third roller 51 in a circumferential direction around the rotation axis R3 so as to be away from one another. When the plurality of convex portions 512 which are arranged in the circumferential direction at the same position in the axial direction are referred to as a convex portion row 513, three convex portion rows 513 are provided in the third roller 51 as shown in FIG. 10. As shown in FIG. 9, the third roller 51 has a heater 514 in its inside which is a convex portion heating part for heating the plurality of convex portions 512.

Figure 11:
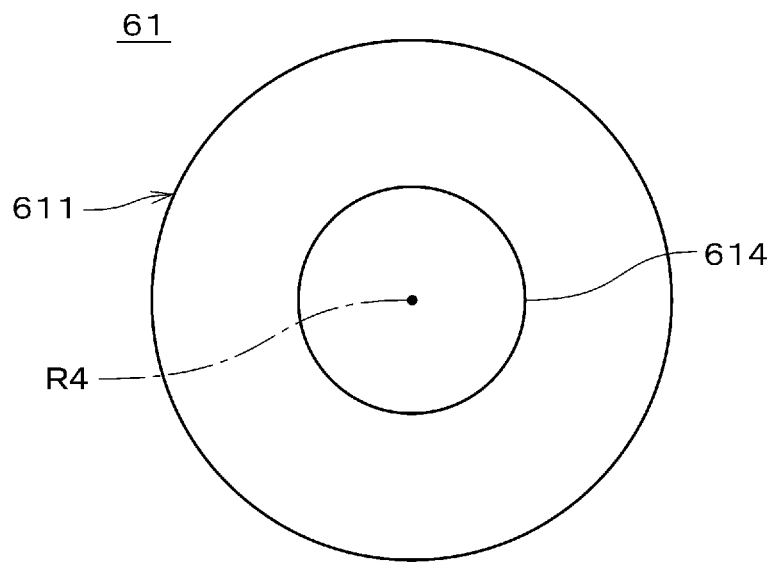
FIG. 11 is a cross-sectional view of a fourth roller.

FIG. 11 is a cross-sectional view of the fourth roller 61, and shows a cross section which is orthogonal to the rotation axis R4. A fourth roller-outer side surface 611 of the fourth roller 61 is a smooth cylindrical surface rotated around the rotation axis R4. The fourth roller 61 has a heater 614 in its inside which is a side surface heating part for heating the fourth roller-outer side surface 611. The first auxiliary bonding roller 63 of the auxiliary bonding part 62 shown in FIG. 1 has a similar structure to the fourth roller 61, and has a heater 634 in its inside.

Figure 12:
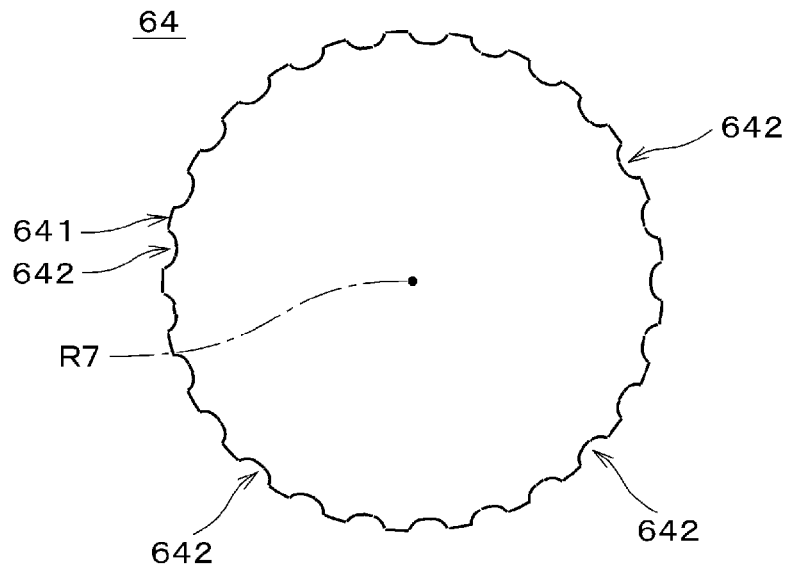
FIG. 12 is a cross-sectional view of a second auxiliary bonding roller.
Figure 13:
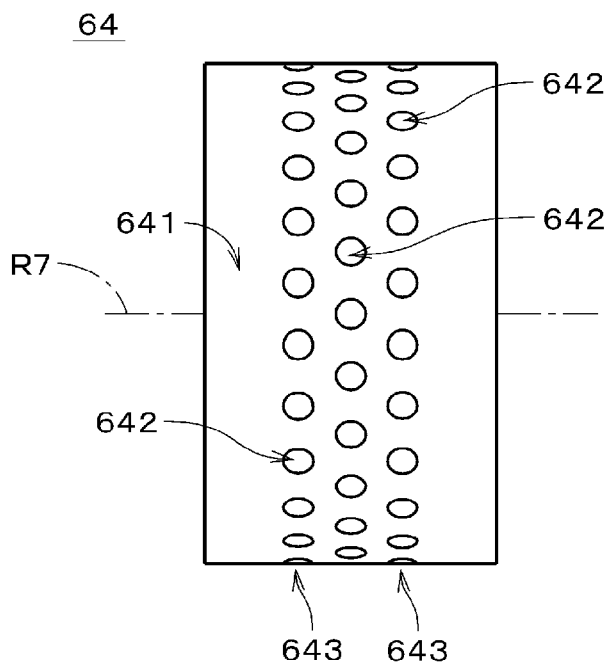
FIG. 13 is a front view of the second auxiliary bonding roller.
Figure 14:
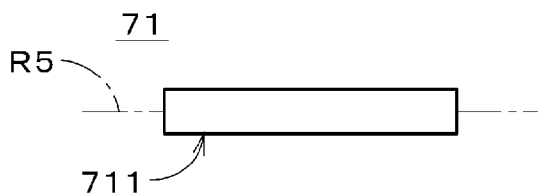
FIG. 14 is a front view of a sheet conveying roller.

FIG. 12 is a cross-sectional view of the second auxiliary bonding roller 64 of the auxiliary bonding part 62, and shows a cross section which is orthogonal to the rotation axis R7. FIG. 13 is a view showing an outer side surface 641 of the second auxiliary bonding roller 64, and in FIG. 13, an appearance of the outer side surface 641 which is observed along a direction orthogonal to the rotation axis R7 is shown. The second auxiliary bonding roller 64 has a similar structure to the supply cylinder 21, and with respect to each of the plurality of positions in the axial direction, a plurality of auxiliary concave portions 642 are arranged on (in) the outer side surface 641 in a circumferential direction around the rotation axis R7 so as to be apart from each other. When the plurality of auxiliary concave portions 642 which are arranged in the circumferential direction at the same position in the axial direction are referred to as an auxiliary concave portion row 643, three auxiliary concave portion rows 643 are provided in the second auxiliary bonding roller 64 as shown in FIG. 13. FIG. 14 is a front view of the sheet conveying roller 71. A conveying roller-outer side surface 711 of the sheet conveying roller 71 is a smooth cylindrical surface.

In the absorbent sheet manufacturing apparatus 1, the plurality of supply concave portion rows 213 in the supply cylinder 21 (see FIG. 3), the plurality of first concave portion rows 313 in the first roller 31 (see FIG. 5), the plurality of second concave portion rows 413 in the second roller 41 (see FIG. 8), the plurality of convex portion rows 513 in the third roller 51 (see FIG. 10), and the plurality of auxiliary concave portion rows 643 in the second auxiliary bonding roller 64 (see FIG. 13) are located at the same positions in the axial direction, respectively. In addition, diameters of the supply cylinder 21, the first roller 31, the second roller 41, the third roller 51 and the second auxiliary bonding roller 64 are same as each other. And also the pitch of the supply concave portions 212 in the circumferential direction, the pitch of the first concave portions 312 in the circumferential direction, the pitch of the second concave portions 412 in the circumferential direction, the pitch of the convex portions 512 in the circumferential direction and the pitch of the auxiliary concave portions 642 in the circumferential direction are same as each other. In the present embodiment, diameters and capacities of the first concave portion 312, the second concave portion 412 and the auxiliary concave portion 642 are equal to or larger than a diameter and capacity of the supply concave portion 212.

Figure 15:
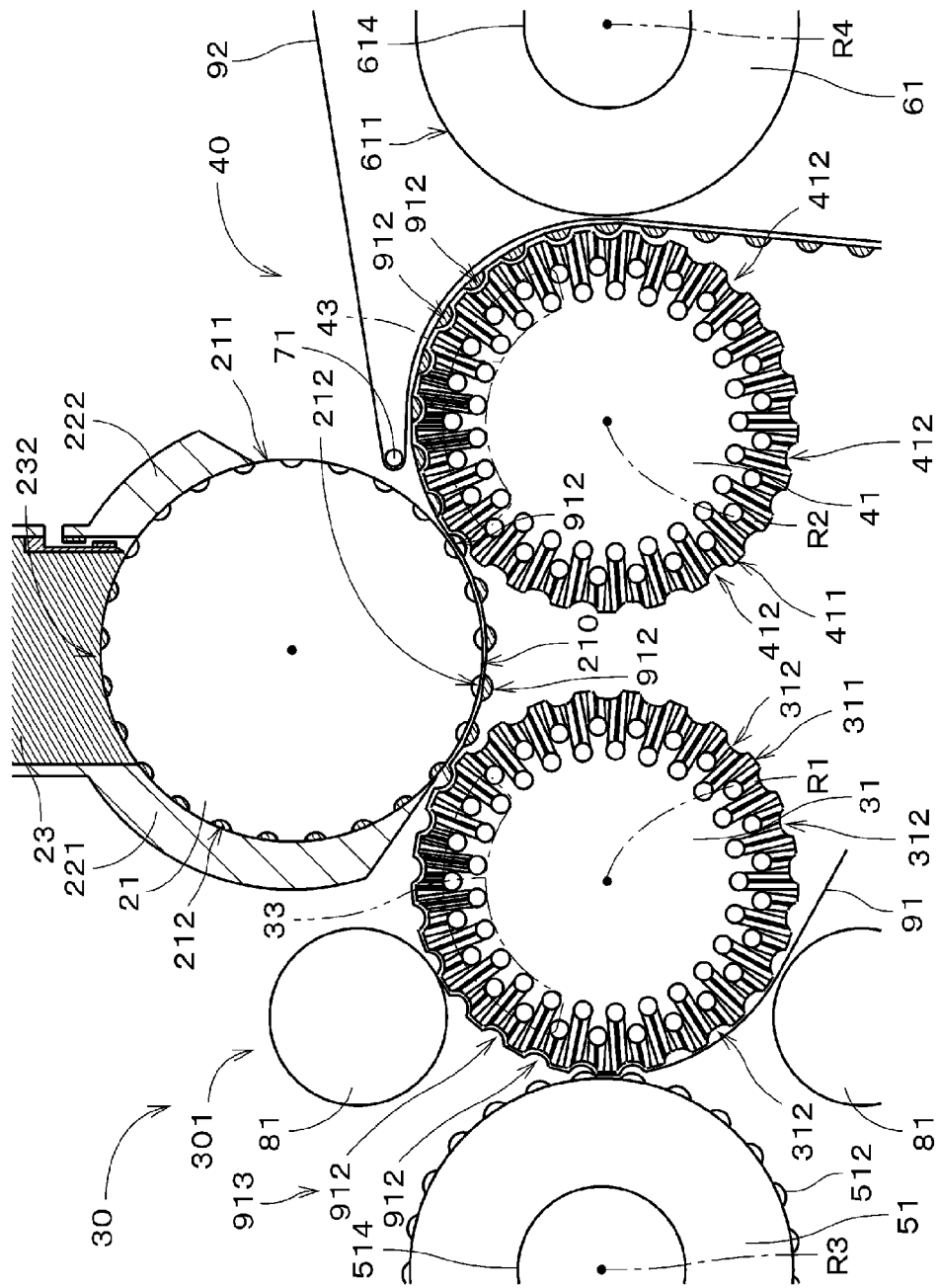
FIG. 15 is a view showing the vicinity of the supply cylinder.

In the manufacture of absorbent sheet by the absorbent sheet manufacturing apparatus 1, as shown in FIG. 15, the first roller 31 is rotated around the rotation axis R1 in the clockwise direction in FIG. 15 to convey the first sheet member 91 on the first roller-outer side surface 311. Also the third roller 51 is rotated around the rotation axis R3 while each convex portion 512 faces (engages) one first concave portion 312 (i.e., the third roller 51 is rotated so that the convex portions 512 sequentially face the first concave portions 312), and the convex portion 512 heated by the heater 514 depresses a portion of the first sheet member 91 toward the first concave portion 312. Therefore, the portion of the first sheet member 91 is dented (is caused to be recessed) into the first concave portion 312 to become a sheet concave portion 912, and the sheet concave portion rows 913 along the conveying direction of the first sheet member 91 are continuously formed on the first sheet member 91.

In the absorbent sheet manufacturing apparatus 1, while the first sheet member 91 is depressed by the plurality of convex portions 512 of the third roller 51, that is, throughout the formation of the sheet concave portion rows 913, the first sheet member 91 is always pressed toward the first roller 31 at both upper and lower sides of a contact position between the first roller 31 and the third roller 51 (i.e., at both sides in the conveying direction of the first sheet member 91) by the two nip rollers 81.

In a region, between the third roller 51 and the supply cylinder 21, of the first roller-outer side surface 311 of the first roller 31, air is suctioned by the first suction parts 33 from the inside of the first roller 31. Therefore, the plurality of sheet concave portions 912 of the first sheet member 91 are suctioned from the inside of the first roller 31 through the plurality of first concave portions 312, and each sheet concave portion 912 is deformed so as to fit in the inner surface of the first concave portion 312, that is, a capacity of the sheet concave portion 912 increases. In FIG. 15, the first sheet member 91 and the second sheet member 92 are drawn so as to be slightly away from the first roller 31, the second roller 41, the supply cylinder 21 and the like in order to facilitate understanding of the drawing.

Here, when constituents for sequentially forming the sheet concave portions of the sheet concave portion rows 913 by denting portions of the first sheet member 91 into first concave portions 312 are referred to as a concave portion forming part 301, the concave portion forming part 301 includes the first suction parts 33, the third roller 51 and the pair of nip rollers 81. The sheet concave portion forming part 30 includes the first roller 31 and the concave portion forming part 301. Since the first roller 31 and the supply cylinder 21 are rotated, (a portion of) the first sheet member 91 on which the sheet concave portion rows 913 are formed by the sheet concave portion forming part 30 is transferred from the first roller-outer side surface 311 of the first roller 31 to the cylinder-outer side surface 211 of the supply cylinder 21.

As mentioned previously, in the supply cylinder 21, particles are sequentially filled from the particle filling part 23 into the plurality of supply concave portions 212. Each supply concave portion 212 filled with particles reaches the lower end of the first cover part 221 with its outer end closed with the first cover part 221 (i.e., the outer end is covered on the cylinder-outer side surface 211). In the following description, a region from the lower end of the first cover part 221 to the lower end of the second cover part 222 with respect to the rotation direction of the supply cylinder 21, is referred to as an "particle supply region 210".

In the absorbent sheet manufacturing apparatus 1, the first roller 31 is rotated while each first concave portion 312 is caused to face (meet) one supply concave portion 212 of the supply cylinder 21 (i.e., the first roller 31 is rotated so that the first concave portions 312 sequentially face the supply concave portions 212 one by one). Thus, the sheet concave portion rows 913 (sheet concave portions 912) of the first sheet member 91 face supply concave portions 212 of the supply cylinder 21 in the particle supply region 210. In this state, the lower portion of the cylinder-outer side surface 211 is in contact with the first sheet member 91, and therefore particles are sequentially supplied from the plurality of supply concave portions 212 into the plurality of the sheet concave portions 912 of the sheet concave portion rows 913. Each supply concave portion 212 which has supplied a sheet concave portion 912 with particles passes through the particle supply region 210, and is moved to the upper portion of the supply cylinder 21 with its outer end closed by the second cover part 222, to go toward the particle filling opening 232 of the particle filling part 23.

The first sheet member 91 (a portion of the first sheet member 91) whose sheet concave portion rows 913 have been supplied with particles is transferred from the cylinder-outer side surface 211 of the supply cylinder 21 to the second roller-outer side surface 411 of the second roller 41 by the second roller 41 rotating around the rotation axis R2. At this time, each second concave portion 412 faces a supply concave portion 212 (i.e., the second concave portions 412 sequentially face the supply concave portions 212 one by one) while the second roller 41 is rotated, so that each sheet concave portion 912 holding the particles is put in a second concave portion 412. In a region, between the supply cylinder 21 and the fourth roller 61, of the second roller-outer side surface 411, air is suctioned by the second suction parts 43 from the inside of the second roller 41. Therefore, the plurality of sheet concave portions 912 of the first sheet member 91 are suctioned from the inside of the second roller 41 through the plurality of second concave portions 412, and each sheet concave portion 912 is held by suctioning so as to fit on the inner surface of the second concave portion 412. In the present embodiment, the second suction parts 43 are also included in the sheet bonding part 40.

On the other hand, the second sheet member 92 on which adhesive is applied is led to the second roller 41 through the sheet conveying roller 71, and on the second roller-outer side surface 411, the second sheet member 92 is placed on the sheet concave portion rows 913 (on the openings of the sheet concave portions 912) of the first sheet member 91 supplied with particles. Then, the first sheet member 91 and the second sheet member 92 overlapping with each other are sandwiched between the second roller 41 and the fourth roller 61 where the fourth roller-outer side surface 611 is heated by the heater 614, so that the first sheet member 91 and the second sheet member 92 are bonded with each other.

Figure 16:
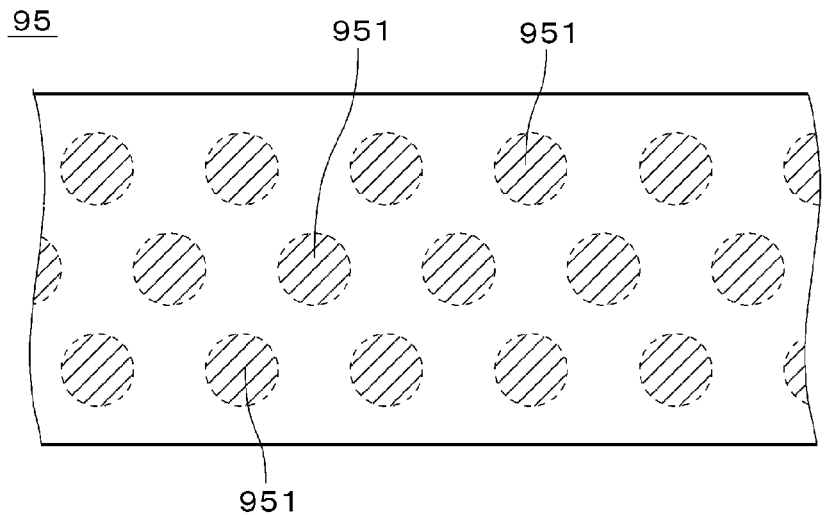
FIG. 16 is a plain view of an absorbent sheet.

The first sheet member 91 and the second sheet member 92 bonded with each other are led to the auxiliary bonding part 62 shown in FIG. 1, and are sandwiched between the first auxiliary bonding roller 63 and the second auxiliary bonding roller 64. At this time, the plurality of sheet concave portions 912 are put in the plurality of auxiliary concave portions 642 of the second auxiliary bonding roller 64 (see FIGS. 12 and 13). Therefore, deformation of sheet concave portions 912 is prevented. In the auxiliary bonding part 62, the outer side surface of the first auxiliary bonding roller 63 is heated by the heater 634, and the first sheet member 91 and the second sheet member 92 are sandwiched between the first auxiliary bonding roller 63 and the second auxiliary bonding roller 64 to be bonded more firmly. Therefore, as shown in FIG. 16, an absorbent sheet 95 having a plurality of particle existence regions 951 arranged in a dotted pattern is formed. In each particle existence region 951, particles of high-absorbent resin are distributed (existing), and the first sheet member 91 and the second sheet member 92 are bonded at regions other than the plurality of particle existence regions 951 (around each particle existence region 951).

As described above, in the absorbent sheet manufacturing apparatus 1, the sheet concave portion rows 913 are formed on the first sheet member 91 by the sheet concave portion forming part 30. The cylinder-outer side surface 211 of the supply cylinder 21 is in contact with the first sheet member 91 while the sheet concave portion rows 913 face the supply concave portions 212. Therefore, particles can be supplied accurately into each sheet concave portion 912 included in the sheet concave portion rows 913 and be held in the sheet concave portion 912 while the particles are practically prevented from scattering to the outside of the sheet concave portion 912.

In the sheet concave portion forming part 30, since the plurality of convex portions 512 of the third roller 51 depress portions of the first sheet member 91 toward the first concave portions 312 of the first roller 31, the sheet concave portion rows 913 can be formed easily. By the heater 514 heating the plurality of convex portions 512, deformation of the first sheet member 91 can be easily performed in the depression by the convex portions 512. As a result, the sheet concave portion rows 913 can be formed more easily. Furthermore, the first sheet member 91 is pressed by the two nip rollers 81 (a pair of nip rollers 81) toward the first roller 31 at both sides of the contact position between the first roller 31 and the third roller 51, and therefore displacement of the first sheet member 91 in the conveying direction can be reduced (suppressed) or prevented in the depression of the first sheet member 91 by the convex portions 512.

In the sheet concave portion forming part 30, since the first sheet member 91 is suctioned by the first suction parts 33 through the plurality of first concave portions 312, the sheet concave portion rows 913 formed in the plurality of first concave portions 312 can be maintained. In addition, each sheet concave portion 912 of the sheet concave portion rows 913 suits the shape of the inner surface of the first concave portion 312. This makes it possible to increase the capacity of each sheet concave portion 912 and equalize the shapes of the sheet concave portions 912.

In the sheet bonding part 40, the sheet concave portion rows 913 are disposed in the second concave portions 412 of the second roller 41. Therefore, each sheet concave portion 912 holding particles can be prevented from deforming on the second roller 41, and the particles in the sheet concave portion 912 can be prevented from scattering around. Since the first sheet member 91 is suctioned by the second suction parts 43 through the plurality of second concave portions 412, the sheet concave portion rows 913 can be easily held in the plurality of second concave portions 412. In addition, the particles in each sheet concave portion 912 can be prevented from scattering around. Furthermore, the first sheet member 91 and the second sheet member 92 overlapping with each other are placed (sandwiched) between the second roller 41 and the fourth roller 61. This allows the first sheet member 91 and the second sheet member 92 to be bonded easily and securely.

Figure 17:
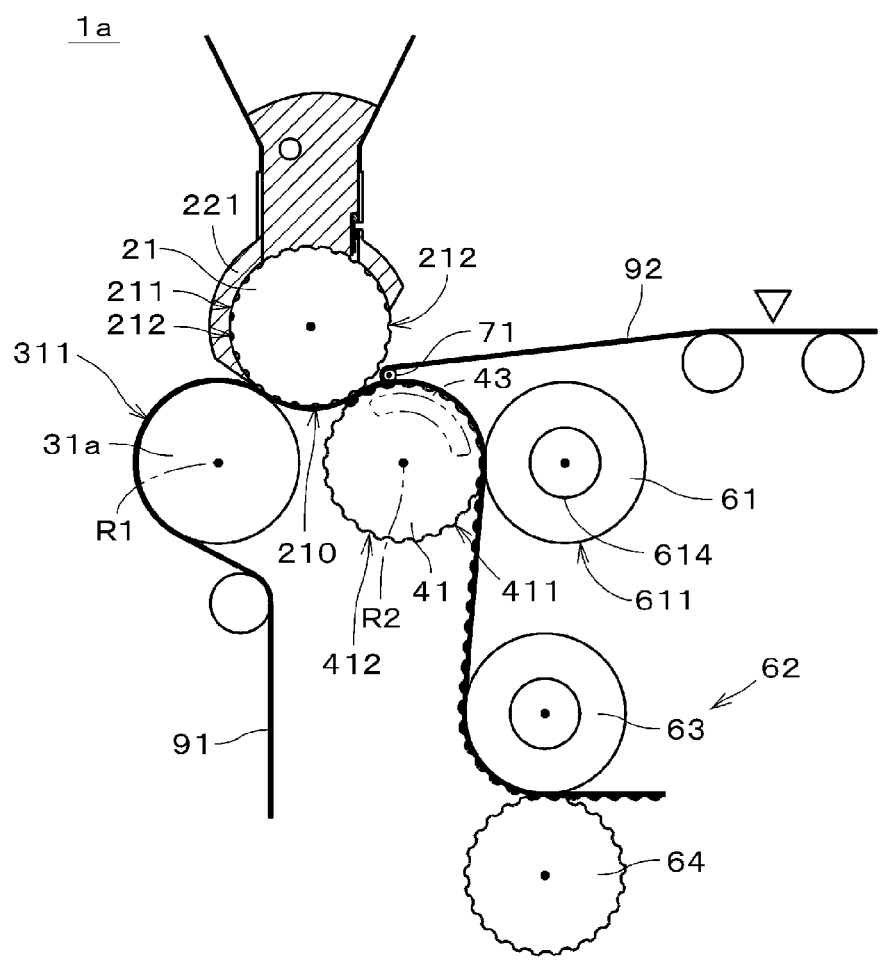
FIG. 17 is a view showing an absorbent sheet manufacturing apparatus in accordance with a second preferred embodiment.

Next, discussion will be made on an absorbent sheet manufacturing apparatus in accordance with a second preferred embodiment of the present invention. FIG. 17 is a view showing an absorbent sheet manufacturing apparatus 1*a* in accordance with the second preferred embodiment. In the absorbent sheet manufacturing apparatus 1*a*, a first roller 31*a* whose first roller-outer side surface 311 is a generally cylindrical and smooth surface, is provided as substitute for the first roller 31 in FIG. 1. Also the concave portion forming part 301 for forming the sheet concave portion rows 913 on the first sheet member 91, that is, the third roller 51, the nip rollers 81 and the first suction parts 33 are removed. The other constituent elements are same as those of the absorbent sheet manufacturing apparatus 1 shown in FIG. 1, and the same elements are denoted by the same reference signs in the following description.

In the manufacture (production) of absorbent sheet by the absorbent sheet manufacturing apparatus 1*a*, the first roller 31*a* is rotated around the rotation axis R1 in the clockwise direction in FIG. 17, and therefore the first sheet member 91 is transferred from the first roller-outer side surface 311 of the first roller 31*a* to the cylinder-outer side surface 211 of the supply cylinder 21. In the supply cylinder 21, each supply concave portion 212 filled with particles reaches the lower end of the first cover part 221 with its outer end closed with the first cover part 221, and the lower portion (the portion including the supply concave portion 212) of the cylinder-outer side surface 211 comes into contact with the first sheet member 91 in the particle supply region 210. Therefore, particles are sequentially supplied from the plurality of supply concave portions 212 onto the first sheet member 91. On the first sheet member 91, particles supplied from the plurality of supply concave portions 212 are arranged in a dotted pattern. In the following discussion, a plurality of regions of the first sheet member 91 on which particles are disposed are referred to as "particle-disposed regions".

The first sheet member 91 which has been supplied with particles is transferred from the cylinder-outer side surface 211 of the supply cylinder 21 to the second roller-outer side surface 411 of the second roller 41 by the second roller 41 rotating around the rotation axis R2. At this time, each second concave portion 412 faces a supply concave portion 212 (i.e., each second concave portion 412 faces a particle-disposed region) while the second roller 41 is rotated. Also the first sheet member 91 is suctioned by the second suction parts 43 from the inside of the second roller 41 through the second suction ports 414 (see FIGS. 7 and 8). Therefore, the particle-disposed regions arranged on the first sheet member 91 in a dotted pattern are put in the second concave portions 412 together with the particles. The particles on the particle-disposed regions are held by suctioning through the first sheet member 91 and the second suction ports 414.

On the other hand, the second sheet member 92 on which adhesive is applied is led to the second roller 41 through the sheet conveying roller 71, and on the second roller-outer side surface 411 of the second roller 41, the second sheet member 92 is overlaid on the first sheet member 91 supplied with the particles. Then, the first sheet member 91 and the second sheet member 92 overlapped with each other are sandwiched between the second roller 41 and the fourth roller 61 where the fourth roller-outer side surface 611 is heated by the heater 614, so that the first sheet member 91 and the second sheet member 92 are bonded with each other. The first sheet member 91 and the second sheet member 92 bonded with each other are led to the auxiliary bonding part 62, and are sandwiched between the second auxiliary bonding roller 64 and the first auxiliary bonding roller 63 whose outer side surface is heated, to be bonded more securely. Therefore, as shown in FIG. 16, the absorbent sheet 95 having the plurality of particle existence regions 951 arranged in a dotted pattern is formed.

In the absorbent sheet manufacturing apparatus 1*a* in accordance with the second preferred embodiment, particles are supplied onto the first sheet member 91 while the lower portion of the cylinder-outer side surface 211 of the supply cylinder 21 is in contact with the first sheet member 91. Therefore, particles can be disposed on the first sheet member 91 in a desired dotted pattern. The second roller 41 is rotated while each second concave portion 412 provided with the second suction ports 414 faces one particle-disposed region of the first sheet member 91. This makes it possible to bond the first sheet member 91 and the second sheet member 92 while particles arranged in a dotted pattern are held in the plurality of second concave portions 412. Therefore, the absorbent sheet where particles are arranged in a desired dotted pattern can be produced easily.

Figure 18:
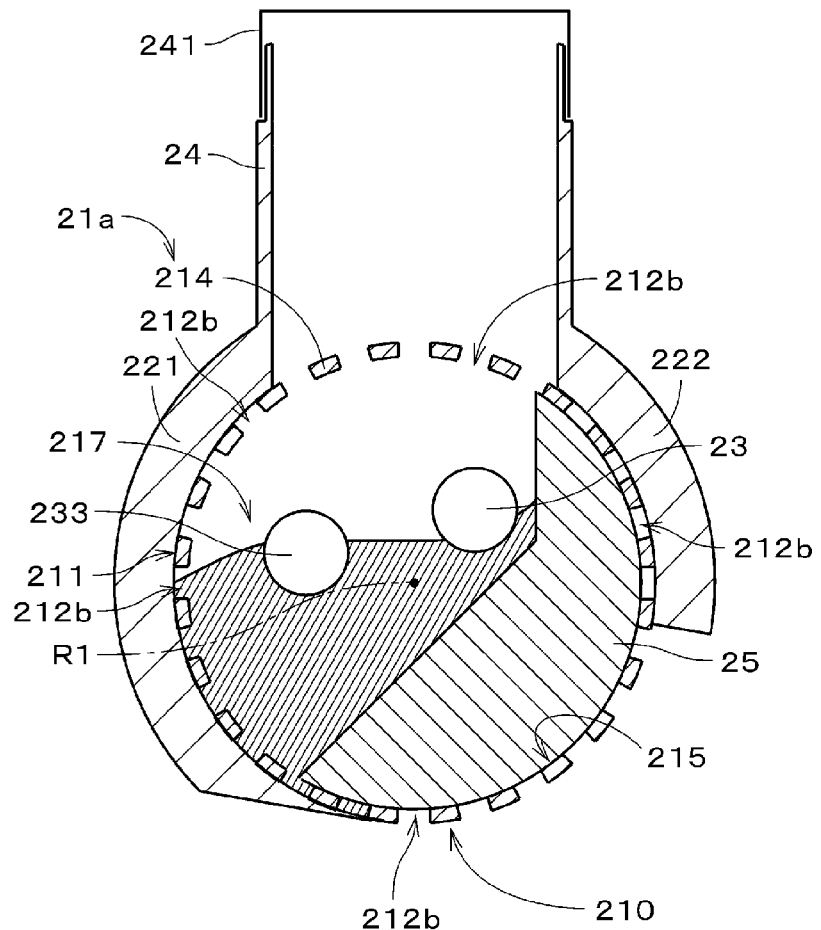
FIG. 18 is a view showing another example of supply cylinder.
Figure 19:
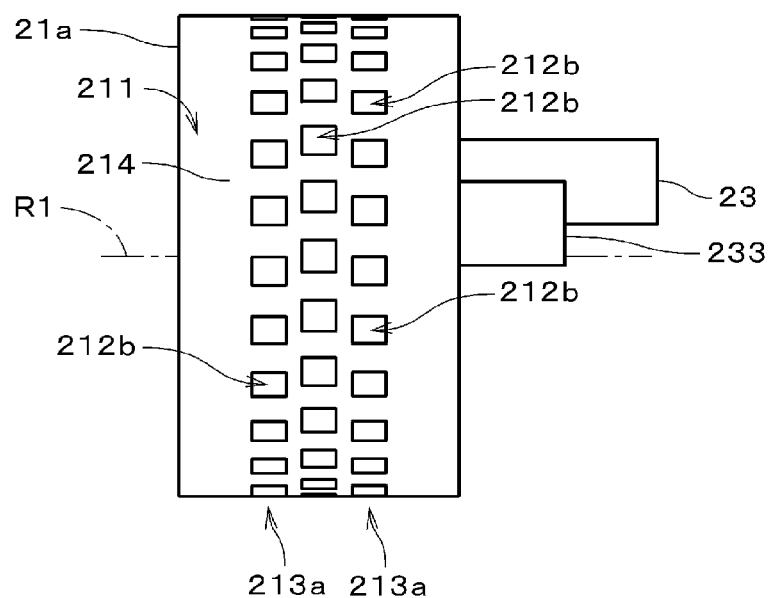
FIG. 19 is a front view of the supply cylinder.

In the absorbent sheet manufacturing apparatus 1 in accordance with the first preferred embodiment, a supply cylinder having a structure different from that of the above supply cylinder 21 may be provided. FIG. 18 is a cross-sectional view showing another example of supply cylinder. FIG. 18 shows a cross section which is orthogonal to the rotation axis R1 of a supply cylinder 21*a*, and in FIG. 18, constituents on the near side of the cross section are also drawn. FIG. 19 is a view showing the cylinder-outer side surface 211 of the supply cylinder 21*a*, and in FIG. 19, an appearance of the cylinder-outer side surface 211 of the supply cylinder 21*a* which is observed along a direction orthogonal to the rotation axis R1 is shown.

As shown in FIGS. 18 and 19, the supply cylinder 21a is a generally cylindrical member around the rotation axis R1, and has a ring-like side wall 214. The supply cylinder 21a is rotated around the rotation axis R1 by driving a belt wound around the cylinder-outer side surface 211 in the circumferential direction. As shown in FIG. 18, a cylindrical exhaust part 24 is provided above the supply cylinder 21a as substitute for the particle filling part 23 in FIG. 1, and an upper opening of the exhaust part 24 is covered with a pouched filter 241 formed of nonwoven fabric or the like. The first cover part 221 and the second cover part 222 similar to those in FIG. 1 are provided around the supply cylinder 21a. In FIG. 19, the first cover part 221 and the second cover part 222 are omitted.

As shown in FIGS. 18 and 19, the supply cylinder 21a has a plurality of through-holes 212b which are holes passing through the side wall 214. The plurality of through-holes 212b are arranged at regular intervals in the circumferential direction around the rotation axis R1 with respect to each of a plurality of positions in the axial direction. As shown in FIG. 19, three through-hole rows 213a (i.e., one through-hole row is the plurality of through-holes 212a which are arranged in the circumferential direction at the same position in the axial direction) are provided in the supply cylinder 21a. In the present embodiment, the shape of each through-hole 212b is generally rectangular, however the through-holes 212b may have a various shape (for example, generally circular shape). In the supply cylinder 21a, one, two, four or more through-hole rows 213a may be provided. In each through-hole row 213a, the through-holes 212b are not necessarily arranged at regular intervals.

As shown in FIG. 18, an isolation part 25 which covers a portion of an inner side surface 215 of the side wall 214 of the supply cylinder 21a is provided in the internal space of the supply cylinder 21a. The isolation part 25 is provided in the right portion of the internal space in FIG. 18 and covers the right portion of the inner side surface 215 from the vicinity of the lowermost portion of the supply cylinder 21a to the vicinity of the uppermost portion. An outer surface of the isolation part 25 (i.e., a surface facing the inner side surface 215 of the supply cylinder 21a) faces the lower end portion of the first cover part 221, the whole particle supply region 210 and the whole second cover part 222.

In the supply cylinder 21a, a portion of the internal space where the isolation part 25 doesn't exist is a particle storage space 217 which stores particles of high-absorbent resin. In FIG. 18, (regions of) the particles are densely hatched. The lower portion of the inner surface of the isolation part 25 goes downward while approaching the lower portion of the first cover part 221. Thus, the particles in the particle storage space 217 move along the inner surface of the isolation part 25 toward the inner side surface 215 of the supply cylinder 21a. The isolation part 25 is provided across almost the entire width of the inner side surface 215 of the supply cylinder 21a in the axial direction, so that through-holes 212b in a region of the inner side surface 215 which is covered with the isolation part 25 are isolated from the particle storage space 217. Thus, also in the particle supply region 210, through-holes 212b are isolated from the particle storage space 217.

A particle replenishment part 23 and a level sensor 233 are provided to the right side of the supply cylinder 21a in FIG. 19. The level sensor 233 is a light-receiving, ultrasonic or contact sensor. The particle replenishment part 23 is a screw feeder which has a screw therein, and replenishes particles into the particle storage space 217 of the supply cylinder 21a from one end portion (right end portion in FIG. 19) of the supply cylinder 21a in the axial direction. When the level sensor 233 detects that the amount of particles stored in the particle storage space 217 becomes equal to or less than a certain level, replenishment of particles into the particle storage space 217 is performed. When particles are replenished into the particle storage space 217, air in the particle storage space 217 is exhausted mainly through the exhaust part 24. Even if particles go out into the exhaust part 24 from the supply cylinder 21a, the particles are prevented by the filter 241 from going to the outside.

The replenishment of particles into the particle storage space 217 isn't performed necessarily from one end portion of the supply cylinder 21a in the axial direction. For example, there may be a case where a particle tank storing particles of high-absorbent resin is provided above the supply cylinder 21a as substitute for the above exhaust part 24, and particles in the particle tank fall by gravity into the particle storage space 217 through the plurality of through-holes 212b of the supply cylinder 21a, so that particles are replenished into the particle storage space 217.

In the absorbent sheet manufacturing apparatus, the supply cylinder 21a is rotated at a high speed around the rotation axis R1, so that particles in the particle storage space 217 are filled into through-holes 212b, which face particles stored in the particle storage space 217, out of the plurality of through-holes 212b in the supply cylinder 21a. In other words, a rotating mechanism for rotating the supply cylinder 21a (the above belt and so on) is a particle filling part for sequentially filling particles into the plurality of through-holes 212b. Until each through-hole 212b filled with particles reaches the particle supply region 210 provided in the lower portion of the supply cylinder 21a, the outer end of the through-hole 212b is closed (blocked) with the first cover part 221 (that is, the through-hole 212b is covered on the cylinder-outer side surface 211). The through-hole 212b is moved to a position where the through-hole 212b faces the isolation part 25, and therefore the particles in the through-hole 212b is isolated (separated) from particles in the particle storage space 217.

In the particle supply region 210, the lower portion of the cylinder-outer side surface 211 is in contact with the first sheet member 91 while the sheet concave portion rows 913 (see FIG. 15) of the first sheet member 91 and through-holes 212b of the supply cylinder 21a face each other, so that particles are sequentially supplied from the plurality of through-holes 212b into the plurality of sheet concave portions 912 of the sheet concave portion rows 913. In the supply cylinder 21a, the plurality of through-holes 212b are a plurality of supply concave portions for supplying the sheet concave portion rows 913 with particles. Each through-hole 212b which has supplied particles into the sheet concave portion 912 passes through the particle supply region 210, and is moved to the upper portion of the supply cylinder 21a with the outer end closed with the second cover part 222.

In the absorbent sheet manufacturing apparatus including the supply cylinder 21a of FIGS. 18 and 19, in a similar fashion to the absorbent sheet manufacturing apparatus 1 shown in FIG. 1, the sheet concave portion rows 913 are formed on the first sheet member 91 by the sheet concave portion forming part 30 (see FIG. 1). The cylinder-outer side surface 211 of the supply cylinder 21a is in contact with the first sheet member 91 while the sheet concave portion rows 913 face the supply concave portions 212. Therefore, particles can be supplied accurately into each sheet concave portion 912 included in the sheet concave portion rows 913 and be held in the sheet concave portion 912 while the particles are practically prevented from scattering to the outside of the sheet concave portion 912.

The supply cylinder 21a of FIGS. 18 and 19 may be provided in the absorbent sheet manufacturing apparatus 1a (see FIG. 17) in accordance with the second preferred embodiment. In this case, the lower portion of the cylinder-outer side surface 211 of the supply cylinder 21a is in contact with the first sheet member 91 while particles are supplied onto the first sheet member 91. Therefore, particles (particle-disposed regions) can be arranged in a desired dotted pattern easily on the first sheet member 91.

Though the preferred embodiments of the present invention have been discussed above, the present invention is not limited to the above-discussed preferred embodiments, but allows various variations.

In the absorbent sheet manufacturing apparatus 1 in accordance with the first preferred embodiment, the first suction ports 314 may be provided only in the plurality of the first concave portions 31 in the first roller 31. Even in this case, the sheet concave portion 912 can be deformed so as to fit along the inner surface of the first concave portion 312, and the sheet concave portion rows 913 can be maintained. If the sheet concave portion rows 913 can be easily maintained in the plurality of first concave portions 312, suction by the first suction parts 33 may be omitted. In addition, if the sheet concave portion rows 913 can be formed by only the first suction parts 33 suctioning the first sheet member 91 through the first concave portions 312, depression of the first sheet member 91 by the convex portions 512 of the third roller 51 may be omitted.

In the second roller 41, the second suction ports 414 may be provided only in the plurality of second concave portions 412. Even in this case, deformation of each sheet concave portion 912 on the second roller 41 is prevented, and falling of particles from the sheet concave portion 912 is prevented. If falling of particles from the sheet concave portions 912 doesn't occur in practice, suction from the inside of the second roller 41 through the second concave portions 412 may be omitted. In the sheet bonding part 40, also the second roller 41 may be provided with a heater for heating the second roller-outer side surface 411. There may be a case where the second roller 41 is provided with a heater, and the heater 614 is omitted in the fourth roller 61. In the case where suction through the second concave portions 412 is performed in the second roller 41, it is preferable that the fourth roller 61 is provided with the heater 614 in order to avoid heat loss due to the suction.

In the absorbent sheet manufacturing apparatus 1a in accordance with the second preferred embodiment, the second roller-outer side surface 411 of the second roller 41 isn't necessarily provided with the plurality of second concave portions 412, and the plurality of second suction ports 414 only have to be provided. In this case, the second roller 41 is rotated while the second suction ports 414 faces the sheet concave portions 912, and the second suction parts 43 hold particles supplied on the first sheet member 91 in a dotted pattern by suctioning the particles from the inside of the second roller 41 through the second suction ports 414 and the first sheet member 91. Therefore, arrangement of particles on the first sheet member 91 can be maintained. As a result, the absorbent sheet where particles are arranged in a dotted pattern can be manufactured easily.

In the above absorbent sheet manufacturing apparatus, particles of absorbent material are supplied such as crosslinked partially neutralized polyacrylic acid, hydrolyzed starch-acrylic acid graft polymer, saponified vinyl acetate-acrylic ester copolymer, hydrolyzed acrylonitrile copolymer, crosslinked acrylonitrile copolymer, hydrolyzed acrylamide copolymer, crosslinked acrylamide copolymer, crosslinked cationic monomers, or crosslinked polyamino acid.

Structure of the absorbent sheet manufacturing apparatus may be utilized for a sheet article manufacturing apparatus for manufacturing a deodorant sheet which is a sheet article for an absorbent article such as a disposable diaper or absorbent pad for light incontinence, by supplying particles of deodorant material such as activated carbon, silica, alumina, zeolite, ion-exchange resin, or molecular sieve onto the first sheet member 91.

The constituent elements of above-discussed preferred embodiments and modified examples may be appropriately combined with one another, as long as they are not mutually exclusive.

While the invention has been shown and described in detail, the foregoing description is in all aspects illustrative and not restrictive. It is therefore understood that numerous modifications and variations can be devised without departing from the scope of the invention.

REFERENCE SIGNS LIST 1, 1a Absorbent sheet manufacturing apparatus
21, 21a Supply cylinder
23 Particle filling part
30 Sheet concave portion forming part
31, 31a First roller
33 First suction part
40 Sheet bonding part
41 Second roller
43 Second suction part
51 Third roller
61 Fourth roller
71 Sheet conveying roller
81 Nip roller
91 First sheet member
92 Second sheet member
95 Absorbent sheet
211 Cylinder-outer side surface
212, 212a Supply concave portion
212b Through-hole
301 Concave portion forming part
311 First roller-outer side surface
312 First concave portion
411 Second roller-outer side surface
412 Second concave portion
414 Second suction port
511 Third roller-outer side surface
512 Convex portion
514 Heater
913 Sheet concave portion row
R0 Cylinder rotation axis
R1 to R7 Rotation axis

The invention claimed is:

1. A sheet article manufacturing apparatus for manufacturing a sheet article for an absorbent article, comprising:
a sheet concave portion forming part for sequentially forming sheet concave portions of a sheet concave portion row on a first sheet member along a conveying direction of said first sheet member, said first sheet member being continuous sheet;
a supply cylinder which has a plurality of supply concave portions arranged on a cylinder-outer side surface in a circumferential direction, said supply cylinder being rotated around a cylinder rotation axis along a horizontal direction, a lower portion of said cylinder-outer side surface being in contact with said first sheet member so that each supply concave portion faces a sheet concave portion, to sequentially supply particles of absorbent material of deodorant material from said plurality of supply concave portions to said sheet concave portions of said sheet concave portion row;

a particle filling part for sequentially filling said plurality of supply concave portions with said particles; and a sheet bonding part for placing a second sheet member on said sheet concave portion row which has been supplied with said particles to bond said second sheet member on said first sheet member, said second sheet member being continuous sheet; wherein said sheet concave portion forming part comprises:

a first roller which has a plurality of first concave portions arranged on a first roller-outer side surface in a circumferential direction, said first roller being in contact with said supply cylinder through said first sheet member and being rotated around a rotation axis parallel to said cylinder rotation axis so that each first concave portion faces a supply concave portion, to transfer said first sheet member from said first roller-outer side surface to said cylinder-outer side surface; and a concave portion forming part for sequentially forming said sheet concave portions by causing portions of said first sheet member to be recessed into first concave portions;

said sheet bonding part comprises:

a second roller which has a plurality of second concave portions arranged on a second roller-outer side surface in a circumferential direction, said second roller being in contact with said supply cylinder through said first sheet member where said particles has been supplied in said sheet concave portion row and being rotated around a rotation axis parallel to said cylinder rotation axis so that each second concave portion faces a supply concave portion, to transfer said first sheet member from said cylinder-outer side surface to said second roller-outer side surface, each sheet concave portion which holds particles being disposed in a second concave portion; and a second sheet supplying part for supplying said second sheet member onto said first sheet member positioned on said second roller-outer side surface.

2. The sheet article manufacturing apparatus according to claim 1, wherein said concave portion forming part comprises a suction part for suctioning said first sheet member from the inside of said first roller through said plurality of first concave portions.

3. The sheet article manufacturing apparatus according to claim 1, wherein said concave portion forming part comprises a third roller which has a plurality of convex portions arranged on a third roller-outer side surface in a circumferential direction, said third roller being rotated around a rotation axis parallel to said cylinder rotation axis so that each convex portion faces a first concave portion, to depress a portion of said first sheet member toward said first concave portion by said each convex portion.

4. The sheet article manufacturing apparatus according to claim 3, wherein said third roller comprises a convex portion heating part for heating said plurality of convex portions.

5. The sheet article manufacturing apparatus according to claim 3, wherein said concave portion forming part further comprises two nip rollers for pressing said first sheet member toward said first roller at both sides of a contact position between said first roller and said third roller in a conveying direction.

6. The sheet article manufacturing apparatus according to claim 1, wherein said sheet bonding part further comprises a fourth roller which is rotated around a rotation axis parallel to said cylinder rotation axis, for bonding said first sheet member and said second sheet member with each other by placing said first sheet member and said second sheet member between said fourth roller and said second roller.

7. The sheet article manufacturing apparatus according to claim 1, wherein said sheet bonding part further comprises a suction part for suctioning said first sheet member from the inside of said second roller through said plurality of second concave portions.

8. A sheet article manufacturing apparatus for manufacturing a sheet article for an absorbent article, comprising:

a supply cylinder which has a plurality of supply concave portions arranged on a cylinder-outer side surface in a circumferential direction, said supply cylinder being rotated around a cylinder rotation axis along a horizontal direction, a lower portion of said cylinder-outer side surface being in contact with a first sheet member to sequentially supply particles of absorbent material or deodorant material from said plurality of supply concave portions onto said first sheet member;

a particle filling part for sequentially filling said plurality of supply concave portions with said particles; and a sheet bonding part for placing a second sheet member on particles of absorbent material or deodorant material which has been supplied on said first sheet member by said supply cylinder to bond said second sheet member on said first sheet member, said second sheet member being continuous sheet; wherein said sheet bonding part comprises:

a roller which has a plurality of suction ports arranged on a roller-outer side surface in a circumferential direction and a plurality of concave portions arranged on said roller-outer side surface in said circumferential direction, said plurality of suction ports being formed in said plurality of concave portions, said roller being in contact with said supply cylinder through said first sheet member which has been supplied with said particles and being rotated around a rotation axis parallel to said cylinder rotation axis so that each concave portion faces a supply concave portion, to transfer said first sheet member from said cylinder-outer side surface to said roller-outer side surface;

a suction part for holding said particles by suctioning said particles from the inside of said roller through said suction ports and said first sheet member so that each region of said first sheet member on which particles are disposed is put in a concave portion together with said particles; and a second sheet supplying part for supplying said second sheet member onto said first sheet member positioned on said roller-outer side surface.

9. The sheet article manufacturing apparatus according to claim 2, wherein said sheet bonding part further comprises a suction part for suctioning said first sheet member from the inside of said second roller through said plurality of second concave portions.

10. The sheet article manufacturing apparatus according to claim 3, wherein
said sheet bonding part further comprises a suction part for suctioning said first sheet member from the inside of said second roller through said plurality of second concave portions.

11. The sheet article manufacturing apparatus according to claim 4, wherein
said sheet bonding part further comprises a suction part for suctioning said first sheet member from the inside of said second roller through said plurality of second concave portions.

12. The sheet article manufacturing apparatus according to claim 5, wherein
said sheet bonding part further comprises a suction part for suctioning said first sheet member from the inside of said second roller through said plurality of second concave portions.

13. The sheet article manufacturing apparatus according to claim 6, wherein
said sheet bonding part further comprises a suction part for suctioning said first sheet member from the inside of said second roller through said plurality of second concave portions.

* * * * *